US012521151B2

(12) United States Patent
Biedermann et al.

(10) Patent No.: US 12,521,151 B2
(45) Date of Patent: Jan. 13, 2026

(54) BONE ANCHORING DEVICE

(71) Applicant: BIEDERMANN TECHNOLOGIES GMBH & CO. KG, Donaueschingen (DE)

(72) Inventors: Timo Biedermann, Trossingen (DE); Bernd Fischer, Bräunlingen (DE); Berthold Dannecker, St. Georgen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 645 days.

(21) Appl. No.: 17/900,626

(22) Filed: Aug. 31, 2022

(65) Prior Publication Data

US 2023/0067818 A1 Mar. 2, 2023

Related U.S. Application Data

(63) Continuation of application No. 16/928,804, filed on Jul. 14, 2020, now Pat. No. 11,464,546.
(Continued)

(30) Foreign Application Priority Data

Jul. 18, 2019 (EP) .................................... 19187133

(51) Int. Cl.
*A61B 17/70* (2006.01)
*A61B 17/00* (2006.01)

(52) U.S. Cl.
CPC ...... *A61B 17/7037* (2013.01); *A61B 17/7032* (2013.01); *A61B 2017/00115* (2013.01)

(58) Field of Classification Search
CPC .................. A61B 17/70; A61B 17/7032–7037
See application file for complete search history.

(56) References Cited

U.S. PATENT DOCUMENTS 6,113,601 A 9/2000 Tatar
6,248,105 B1 6/2001 Schläpfer et al.
(Continued)

FOREIGN PATENT DOCUMENTS

CN 1254266 A 5/2000
CN 101664334 A 3/2010
(Continued)

OTHER PUBLICATIONS

Extended European Search Report for European Application No. EP 10 19 6880, Extended European Search Report dated May 12, 2011 and mailed May 20, 2011 (6 pgs.).
(Continued)

*Primary Examiner* — Eduardo C Robert
*Assistant Examiner* — Michelle C Green
(74) *Attorney, Agent, or Firm* — Womble Bond Dickinson (US) LLP

(57) ABSTRACT

A bone anchoring device includes an anchoring element having a shank for anchoring in a bone and a head, a receiving part configured to pivotably receive the head, and a pressure member for exerting pressure on the head to clamp the head in the receiving part, the pressure member defining a head receiving recess for pivotably holding at least a portion of the head therein and comprising a first surface configured to restrict removal of the head from the head receiving recess. The head includes a first position indication structure configured to engage a second position indication structure of the bone anchoring device when the shank assumes a first angular position relative to the receiving part. The first and second position indication structures disengage from one another when the shank is moved out of the first angular position to a different angular position.

20 Claims, 10 Drawing Sheets

Related U.S. Application Data

(60) Provisional application No. 62/875,764, filed on Jul. 18, 2019.

(56) References Cited

U.S. PATENT DOCUMENTS

| | | | | |
|---|---|---|---|---|
| 7,001,389 | B1 | 2/2006 | Navarro et al. | |
| 7,867,258 | B2 | 1/2011 | Drewry et al. | |
| 9,445,847 | B2 | 9/2016 | Biedermann et al. | |
| 9,833,263 | B2 | 12/2017 | Chandanson et al. | |
| 11,464,546 | B2 * | 10/2022 | Biedermann ...... | A61B 17/7037 |
| 2004/0267264 | A1 | 12/2004 | Konieczynski et al. | |
| 2006/0155278 | A1 | 7/2006 | Warnick | |
| 2006/0173456 | A1 | 8/2006 | Hawkes et al. | |
| 2007/0055240 | A1 | 3/2007 | Matthis et al. | |
| 2007/0118117 | A1 | 5/2007 | Altarac et al. | |
| 2008/0015597 | A1 | 1/2008 | Whipple | |
| 2008/0045951 | A1 | 2/2008 | Fanger et al. | |
| 2008/0147121 | A1 | 6/2008 | Justis et al. | |
| 2008/0269809 | A1 | 10/2008 | Garamszegi | |
| 2010/0023061 | A1 * | 1/2010 | Randol ............. | A61B 17/7037 606/301 |
| 2010/0087863 | A1 | 4/2010 | Biedermann et al. | |
| 2010/0160976 | A1 | 6/2010 | Biedermann et al. | |
| 2010/0241175 | A1 * | 9/2010 | Walker ............... | A61B 17/8605 606/301 |
| 2011/0089755 | A1 | 4/2011 | Itano et al. | |
| 2011/0093021 | A1 | 4/2011 | Fanger et al. | |
| 2013/0150852 | A1 | 6/2013 | Shluzas et al. | |
| 2013/0165977 | A1 | 6/2013 | Biedermann et al. | |
| 2015/0012042 | A1 * | 1/2015 | Black ................ | A61B 17/7037 606/269 |
| 2015/0032165 | A1 * | 1/2015 | Harper ............... | A61B 17/8685 606/279 |
| 2016/0106473 | A1 * | 4/2016 | Rezach ............. | A61B 17/7035 29/428 |
| 2016/0278832 | A1 * | 9/2016 | Segawa ............. | A61B 17/7037 |
| 2016/0296256 | A1 * | 10/2016 | Chandanson ...... | A61B 17/8605 |

FOREIGN PATENT DOCUMENTS

| | | | |
|---|---|---|---|
| EP | 2 468 198 | A1 | 6/2012 |
| EP | 2 606 841 | A1 | 6/2013 |
| JP | 2008-526435 | A | 7/2008 |
| WO | WO 2006/076422 | A2 | 7/2006 |
| WO | WO 2008/112114 | A1 | 9/2008 |
| WO | WO 2009/132110 | A1 | 10/2009 |

OTHER PUBLICATIONS

Extended European Search Report for European Application No. EP 19187133.4, dated Jan. 27, 2020, 9 pages.

* cited by examiner

BONE ANCHORING DEVICE

CROSS-REFERENCE TO RELATED APPLICATION(S)

This application is a continuation of U.S. patent application Ser. No. 16/928,804, filed Jul. 14, 2020, which claims priority to and the benefit of U.S. Provisional Patent Application No. 62/875,764, filed Jul. 18, 2019, the contents of which are hereby incorporated by reference in their entirety, and claims priority from European Patent Application EP 19 187 133.4, filed Jul. 18, 2019, the contents of which are hereby incorporated by reference in their entirety.

BACKGROUND

Field

The application relates to a bone anchoring device of the polyaxial type that includes a bone anchor and a receiving part, which permits indication or identification of an angular position of the bone anchor relative to the receiving part.

Description of Related Art

A bone anchoring device of this type is known from U.S. Pat. No. 9,833,263 B2. The bone anchor assembly described therein includes one or more features for indicating the relative positioning of the receiver member and the shank, for example, in the form of a surface feature included in the head of the bone anchor that interacts with a drag ring to provide tactile or audible feedback when the shank is positioned at a particular orientation with respect to the receiver member. In another embodiment, the head of the bone anchor and a compression cap disposed in the receiver member can each include engagement features that cooperate to allow for selective locking of the orientation of the shank with respect to the receiver member.

SUMMARY

In the known bone anchor assembly, an interaction between a head of an anchoring element and a receiver member is required for indicating a special angular position of a shank of the anchoring element relative to the receiver member. Alternatively, when the orientation indication features are provided only on the head and on a separate compression cap, a position of the compression cap is coupled to a position of the shank relative to the receiver member.

It is an object of the invention to provide an improved or alternative bone anchoring device that permits indication or identification of a position of the shank relative to a receiver member.

According to an aspect, a bone anchoring device is provided that includes an anchoring element having a shank for anchoring in bone and a head, a receiving part configured to receive the head of the anchoring element in a pivotable manner, such that the shank can assume a plurality of angular positions including a predetermined angular position relative to the receiving part, the receiving part having a passage defining a central axis, and a pressure member configured to exert pressure onto the head to clamp the head in the receiving part, the pressure member being at least partially arranged in the passage. The head includes a first position indication structure that is configured to engage a second position indication structure of the pressure member, to provide an indication of when the shank is at the predetermined angular position relative to the receiving part. The pressure member has a head receiving recess to receive at least a portion of the head and a section configured to encompass the head in such a manner that the head is held by friction in the head receiving recess.

With a bone anchoring device according to embodiments of the invention, the surgical step of aligning the receiving part relative to an inserted shank when the rod and a fixation element are not yet inserted into the receiving part is better facilitated, as the predetermined angular position can be verified. Other angular positions can be adjusted easily since the head is temporarily held by friction relative to the receiving part.

The predefined angular position may be a position where the shank and the receiving part are coaxial with respect to each other. This position can also be called or considered a "zero position". It may be advantageous for a surgeon to obtain feedback during alignment of the receiving parts relative to the shanks in-situ when the receiving parts and the shanks are in the zero position relative to one another.

With a bone anchoring device according to embodiments of the invention, an interaction to indicate the predefined angular position may be limited to an interaction between only the shank and the pressure member. The receiving part is not involved when the shank is pivoted and enters the predefined angular position. Hence, the indication of the predefined angular position is substantially independent of the clamping of the head in the receiving part.

The feedback may be a tactile feedback, wherein a user feels with his or her hands when the receiving part snaps into the predefined angular position. Moreover, when the receiving part is in the predefined angular position and is then moved away from the predefined angular position, a tactile feedback may be given in the form of a resistance to be overcome.

In one embodiment, the feedback obtained by the user may be an audible feedback, for example, a clicking, when the predefined angular position is assumed. This audible feedback may be caused by the resilient engagement of the first position indication structure and the second position indication structure.

In some embodiments, the first indication structure and/or the second position indication structure is monolithically formed with either the head or the pressure member, respectively. In another embodiment, the first indication structure and/or the second position indication structure is formed as a separate part.

The first and second position indication structures on the head and the pressure member, respectively, may be provided in polyaxial bone anchoring devices of the top-loading type, for example, wherein the bone anchoring element is inserted into the receiving part from a top end thereof, or of the bottom-loading type, for example, where the bone anchoring element is inserted into the receiving part from a bottom end thereof.

According to another aspect, a bone anchoring device is provided that includes an anchoring element having a shank for anchoring in bone and a head, a receiving part configured to receive the head of the anchoring element in a pivotable manner such that the shank can assume a plurality of angular positions including a predetermined angular position relative to the receiving part, the receiving part having a passage defining a central axis, and a pressure member configured to exert pressure onto the head to clamp the head in the receiving part, the pressure member being at least partially arranged in the passage. The head includes a first position indication structure that is configured to engage a second position indication structure of the pressure member, to provide an indication of when the shank is at the predetermined angular position relative to the receiving part. The first position indication structure is configured to engage the second position indication structure in a resilient manner.

The resilient engagement may be particularly suitable for producing a tactile and/or audible feedback signal.

BRIEF DESCRIPTION OF THE DRAWINGS

Further features and advantages will become apparent from the detailed description of embodiments, by means of the accompanying drawings. In the drawings.

DETAILED DESCRIPTION

Figure 1:
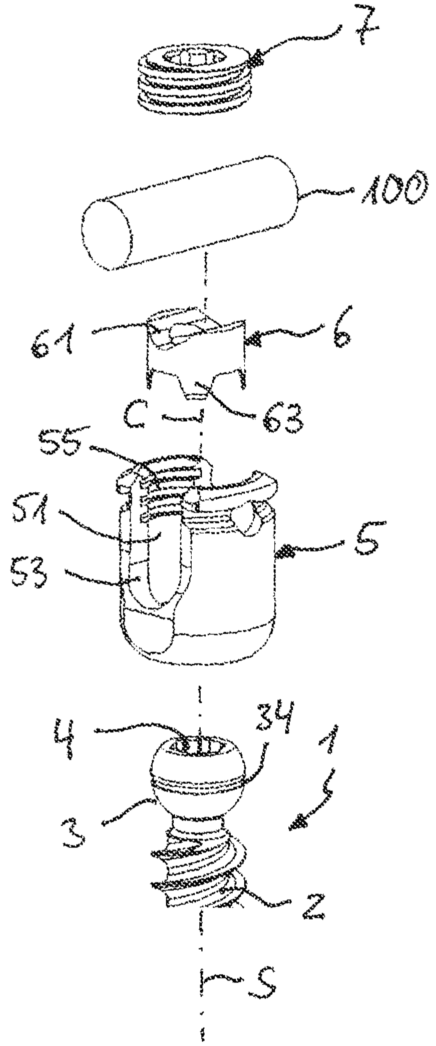
FIG. 1 shows an exploded perspective view of a bone anchoring device according to a first embodiment.
Figure 2:
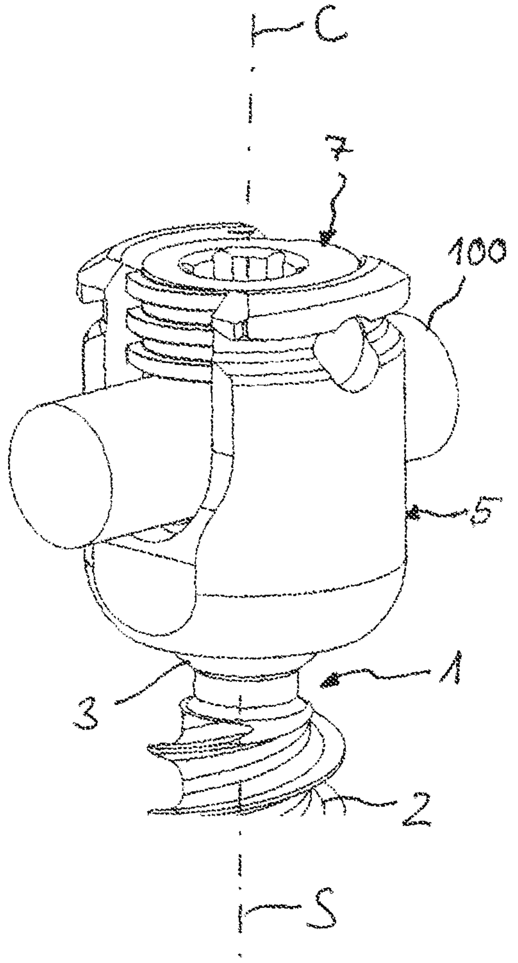
FIG. 2 shows a perspective view of the bone anchoring device of FIG. 1 in an assembled state.
Figure 3:
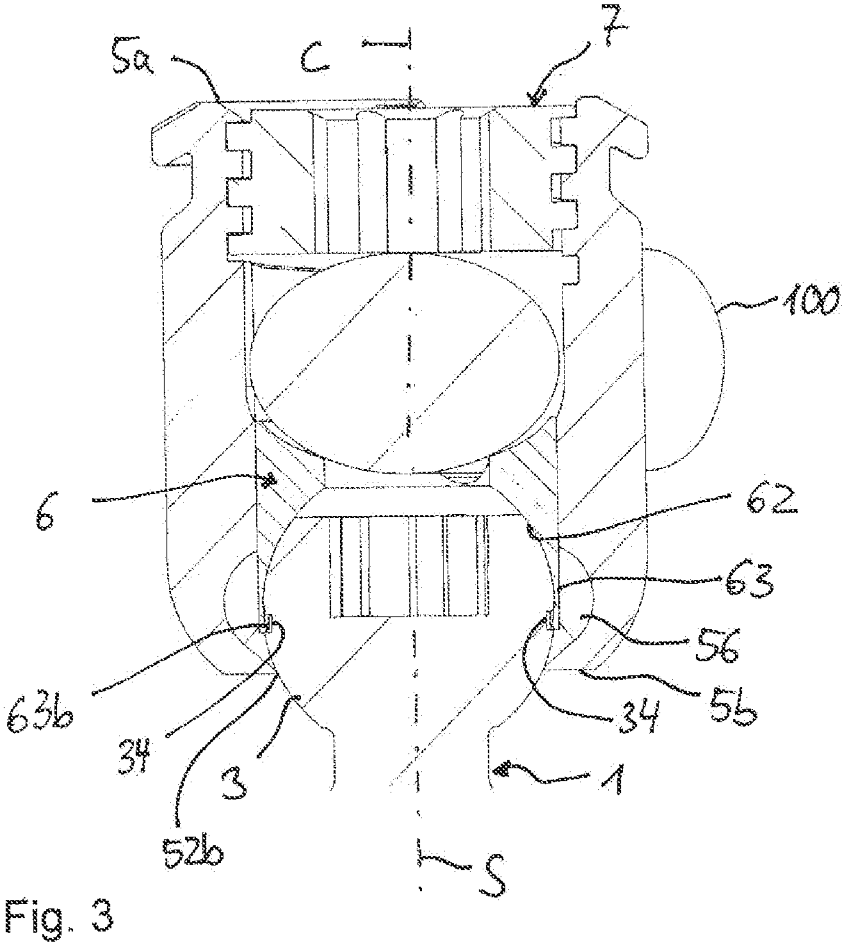
FIG. 3 shows a cross-sectional view of the bone anchoring device of FIGS. 1 and 2, the cross-section taken in a plane that goes through centers of the head, the shank, and the receiving part, and that extends at an angle to a longitudinal axis of an inserted rod.

A polyaxial bone anchoring device according to a first embodiment, which is generally shown in FIGS. 1 to 3, includes a bone anchoring element 1 in the form of a screw member having a threaded shank 2 and a head 3. A shank axis S is defined by the longitudinal axis or screw axis of the shank 2. The head 3 is shaped as a spherical segment that includes a region with the equator or largest diameter E of the sphere (see e.g. FIG. 4*a*). On its free end, the head 3 has a recess 4 for engagement with a tool. The bone anchoring device further includes a receiving part 5 for connecting the bone anchoring element 1 to a rod 100. A pressure member 6 is arranged in the receiving part on top of the head 3. For securing the rod 100 in the receiving part 5 and for exerting pressure onto the head 3, a locking element 7 in the form of, for example, a set screw which cooperates with the receiving part 5, may also be provided.

As shown in particular in FIGS. 3 and 5 to 8, the receiving part 5 is substantially cylindrical and has a first or top end 5*a*, a second or bottom end 5*b*, and a passage 51 extending from the top end 5*a* towards the bottom end 5*b*, the passage defining a longitudinal central axis C. At the bottom end 5*b*, a seat portion 52 is formed for accommodating the head 3. The seat portion 52 may be spherically-shaped with a radius corresponding substantially to a radius of the head 3, so that the head 3 is supported by the seat portion 52 to allow the head 3 to pivot in the seat portion 52, similar to a ball and socket joint. Other shapes of the seat portion that permit pivoting of the head may also be possible. The seat portion 52 further is in communication with the passage 51 and has an opening 52*b* through which shank 2 of the bone anchoring element 1 can extend. An inner diameter of the opening 52*b* is smaller than the greatest diameter E of the head, so that the bone anchoring element is insertable only from the top end 5*a* into the receiving part 5. Hence, the first embodiment shows a top-loading polyaxial bone anchoring device. The passage 51 includes a widened section 51*a* that has an inner diameter that is slightly greater than a largest diameter of the seat portion 52 and a diameter of the upper portion of the passage 51. A substantially U-shaped channel or recess 53 having a longitudinal axis L that coincides with a longitudinal axis of a straight rod 100 when the rod is inserted in the recess extends from the top end 5*a* to a distance therefrom. The substantially U-shaped recess 53 divides the upper portion of the receiving part 5 into two free legs 54 between which the rod 100 is received. An internal thread 55, for example a square thread, is provided at the receiving part 5 adjacent to the top end 5*a* for cooperating with the locking element 7.

In the seat portion 52 and the widened section 51*a*, a plurality of circumferentially distinct recesses 56 are provided. The recesses 56 extend into an inner wall of the receiving part and are substantially spherical-shaped with a radius considerably smaller than the radius of the seat portion 52. For example, as shown in the embodiment, four recesses 56 are arranged in the widened section 51*a* and the seat portion 52. As shown in greater detail in FIGS. 7 and 8, the recesses 56 are arranged pair-wise, such that when viewed along the longitudinal axis L of the substantially U-shaped recess 53, at either end of the receiving part 5, two recesses 56 are respectively arranged on the two sides of the longitudinal axis L. The recesses 56 locally enlarge the width of the seat portion 52, and serve for providing an accommodation space for portions of the pressure member 6, as described in greater detail below.

Furthermore, cut-outs 57 may be formed on either side of the legs 54 which may contribute to a reduced size of the receiving part. Lastly, tool engagement portions 58, such as a circumferential groove and/or central recesses provided at the legs 54, allow engagement of the receiving part 5 with a tool.

Figure 4A:
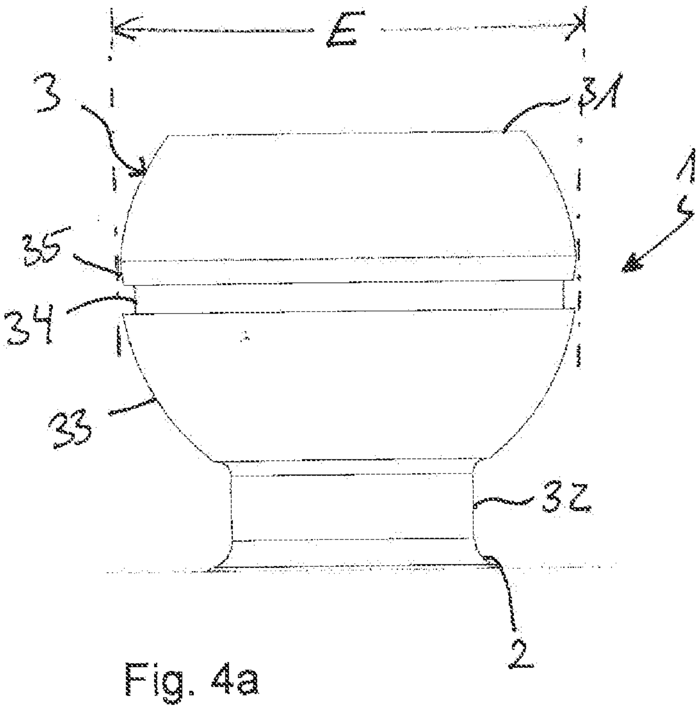
FIG. 4*a* shows an enlarged side view of the head of a bone anchoring element of the bone anchoring device of FIGS. 1 to 3.
Figure 4B:
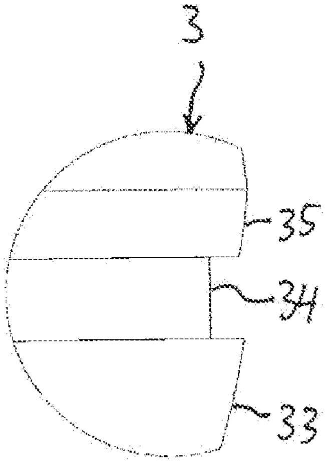
FIG. 4*b* shows an enlarged view of a detail of FIG. 4*a*.
Figure 5:
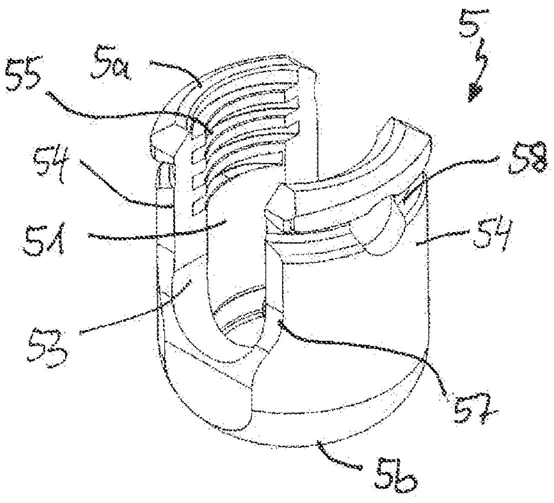
FIG. 5 shows a perspective view from a top of a receiving part of the bone anchoring device of FIGS. 1 to 3.
Figure 6:
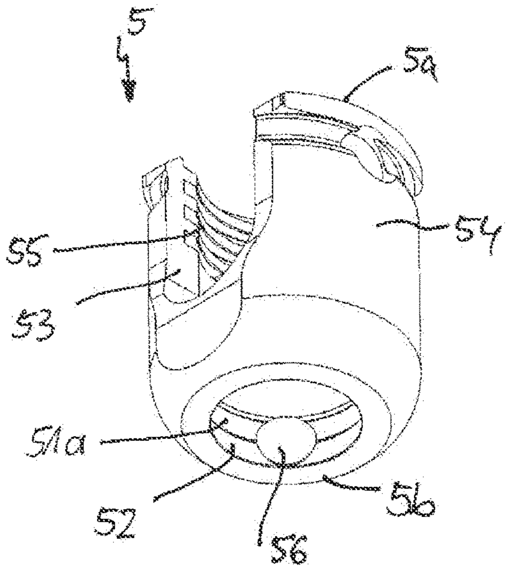
FIG. 6 shows a perspective view from a bottom of the receiving part of FIG. 5.
Figure 7:
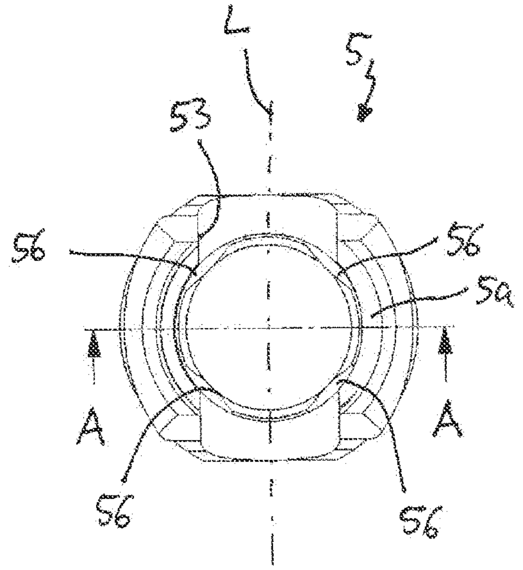
FIG. 7 shows a top view of the receiving part of FIGS. 5 and 6.
Figure 8:
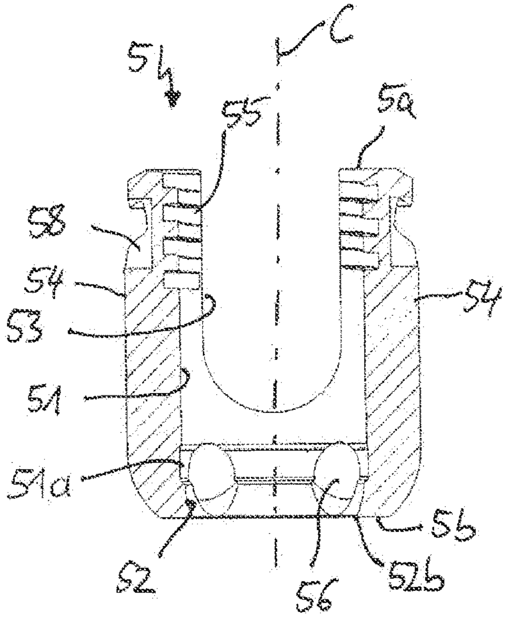
FIG. 8 shows a cross-sectional view of the receiving part of FIGS. 5 to 7, the cross-section taken along line A-A in FIG. 7.
Figure 9:
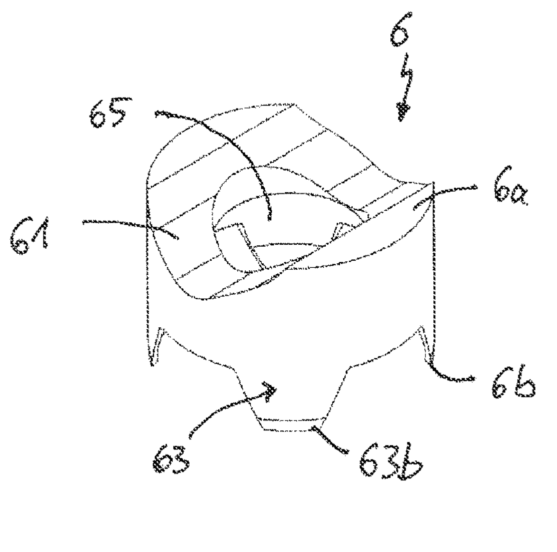
FIG. 9 shows a perspective view from a top of a pressure member of the bone anchoring device according to the first embodiment of FIGS. 1 to 3.
Figure 10:
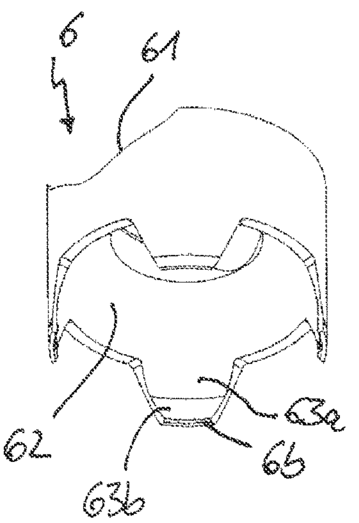
FIG. 10 shows a perspective view from a bottom of the pressure member of FIG. 9.
Figure 11:
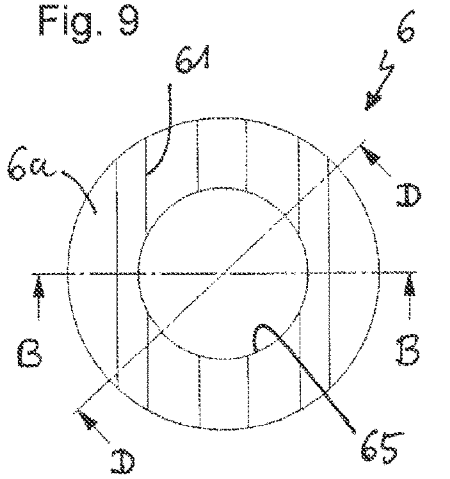
FIG. 11 shows a top view of the pressure member of FIGS. 9 and 10.
Figure 12:
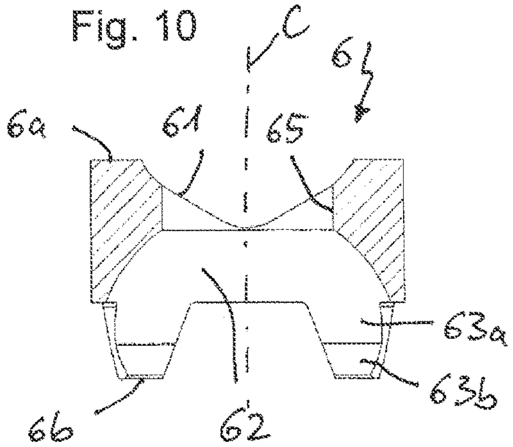
FIG. 12 shows a cross-sectional view of the pressure member of FIGS. 9 to 11, the cross-section taken along line B-B in FIG. 11.
Figure 13:
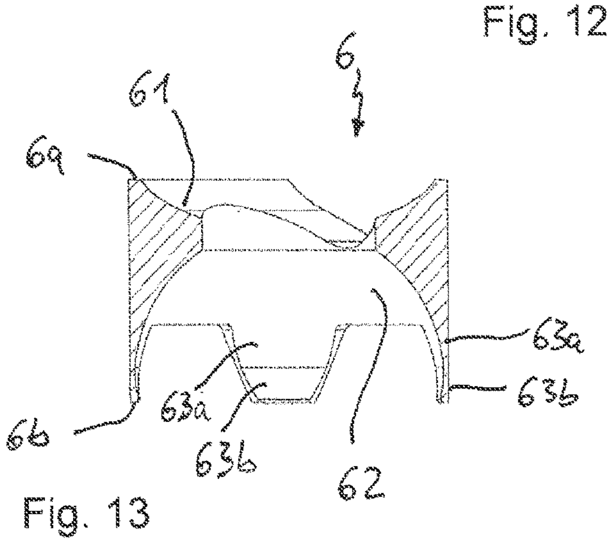
FIG. 13 shows a cross-sectional view of the pressure member of FIGS. 9 to 12, the cross-section taken along line D-D in FIG. 11.

Referring in greater detail to FIGS. 4*a* and 4*b*, the head 3 has the shape of a segment of a sphere, or in other words, the shape of a truncated sphere. In greater detail, on the side opposite to the shank 2, the head 3 has a substantially flat end surface 31 in which the recess 4 for engagement with a tool is provided. On the opposite side, the head joins with a neck 32, which has a smaller diameter than the diameter of the head 3 adjacent to the neck 32. The neck may be cylindrical and thread-free. Between the surface 31 and the neck 32, the head 3 has a substantially spherically-shaped outer surface 33. In the spherical outer surface 33, a circumferentially extending groove 34 is formed that may be located in an axial direction at approximately a region including the equator or greatest diameter E of the head 3. The groove 34 forms a first position indication structure, which is configured to cooperate with a second position indication structure provided at a pressure member 6. The groove 34 extends around the entire head 3. However, in some embodiments, a groove may instead be formed only at specific circumferential positions that correspond to the positions of the second position indication structure on the pressure member 6. As the groove 34 runs perpendicular to the central axis C, the groove defines a zero position as a predefined angular position of the shank, where the zero position is a position where the shank axis S is substantially coaxial with the longitudinal axis C of the receiving part. A cross-section and a depth and/or width of the groove 34 may be such that a portion of the second position indication structure of the pressure member 6 can be accommodated therein. Moreover, the size and shape of the groove 34 is such that the second position indication structure of the pressure member 6 is able to remain engaged with the groove 34 when the shank 2 is at the zero position. In other words, the engagement can be released only if the head 3 is pivoted relative to the pressure member 6. In the embodiment shown, the cross-section of the groove 34 is rectangular.

Between the end surface 31 and the groove 34, and adjacent to the groove 34, a small reduced diameter section 35 may be formed which narrows towards the groove 34. For example, the reduced diameter section 35 may be conically shaped. The reduced diameter section 35 may facilitate the engagement of the groove 34 with the second position indication structure.

The pressure member 6 may be formed monolithically, and may be substantially cylindrical with an outer diameter which allows movability in the axial direction in the passage 51 of the receiving part. In greater detail, the pressure member 6 has a first or top end 6*a* and a second or bottom end 6*b*. At the top end 6*a*, a rod receiving recess 61 is formed that provides a rod support surface. A base section of the recess 61 may have a substantially V-shaped cross-section, with a longitudinal axis extending substantially perpendicular to the cylinder axis of the pressure member 6 and to the central axis C of the receiving part. A depth of the recess 61 may be smaller than a diameter of the rod 100. Hence, once the rod 100 rests on the support surface, the rod projects over the top end 6*a* of the pressure member.

At the bottom end 6*b* of the pressure member, a head receiving recess in the form of a substantially spherical recess 62 is provided for receiving the head 3 therein. The radius of the spherical recess 62 can be slightly larger than the radius of the head 3, so that the head 3 fits easily into the recess 62. At the bottom end 6*b*, cut-outs arranged substantially in a circumferential direction form projections or flaps 63. The flaps 63 form a second position indication structure that can engage the groove 34 of the head 3 when the shank 2 assumes the predetermined position relative to the receiving part 5. Due to their shape and size, the flaps 63 are flexible to some extent, they can be expanded and compressed in the radial direction.

In the embodiment described, there are four cut-outs and four flaps, but in other embodiments, any other suitable number of flaps may be provided. The flaps 63 have an approximate V-shape when seen from a side-view, with the tip of the V-shape truncated. The flaps 63 are arranged to the left side and to the right side of the rod receiving recess 61, near the ends thereof, corresponding to the locations of the recesses 56 in the receiving part when the pressure member 6 is arranged in the receiving part 5 and the rod receiving recess 61 and the substantially U-shaped recess 53 are aligned. A length of the flaps 63 and a depth of the spherical recess 62 is such that the flaps 63 extend beyond the area of the spherical head 3 with the largest outer diameter E when the pressure member 6 is mounted to the head 3. Each of the flaps 63 has a first spherical section 63*a* adjacent to the spherical recess 62 and a second spherical section 63*b* extending from the first spherical section 63*a* to the free end of the flap 63. An inner diameter of the first spherical section 63*a* is the same as or is greater than the outer diameter of the spherical outer surface portion 33 of the head 3 that comes into contact therewith. The inner diameter of the second spherical section 63*b* may be slightly smaller than the largest outer diameter E of the spherical surface portion 33 of the head 3. As a result, the pressure member 6 has a slight undersize with respect to the head 3 at least in the region of the second spherical section 63*b* of the flaps 63.

Figure 14A:
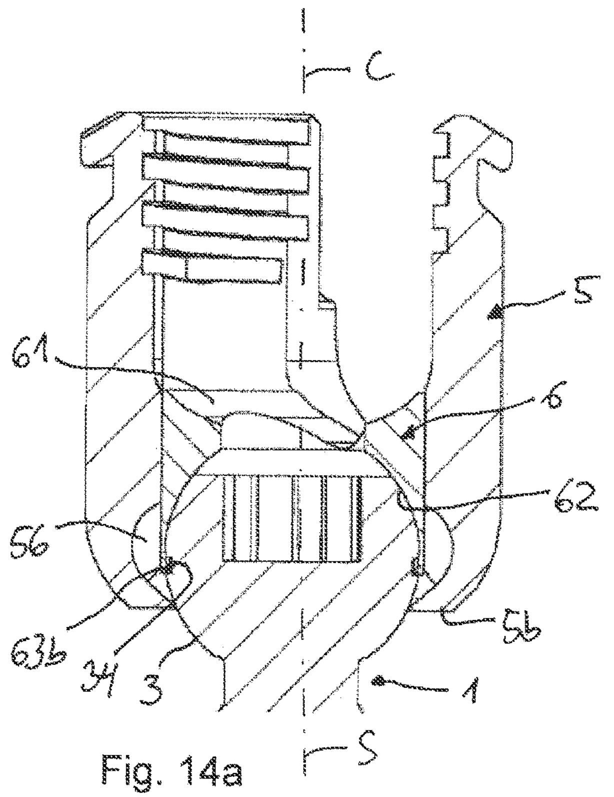
FIG. 14*a* shows a cross-sectional view of the bone anchoring device of FIGS. 1 to 3, when the shank is at a predefined angular position relative to the receiving part.
Figure 14B:
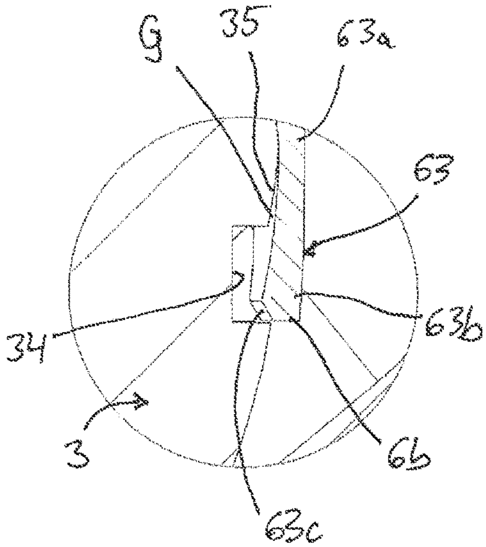
FIG. 14*b* shows an enlarged view of a detail of FIG. 14*a*.
Figure 15A:
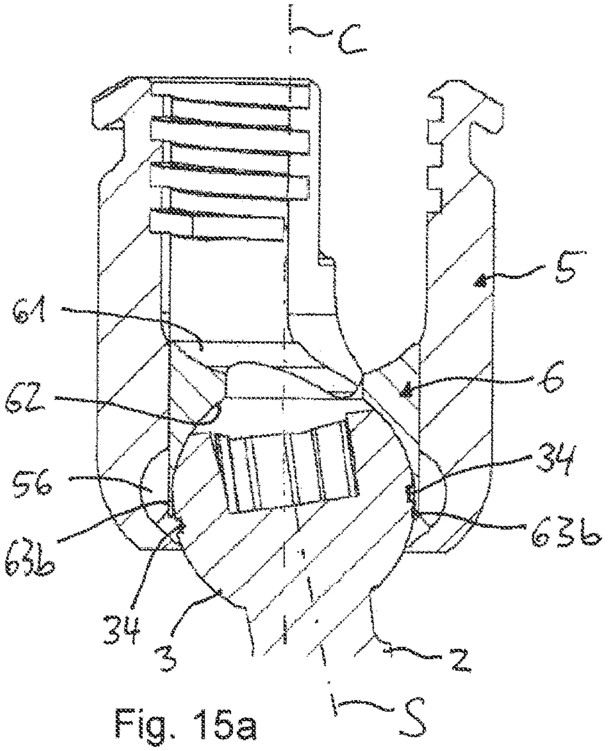
FIG. 15*a* shows a cross-sectional view of the bone anchoring device of FIGS. 1 to 3, when the shank is at another angular position relative to the receiving part.
Figure 15B:
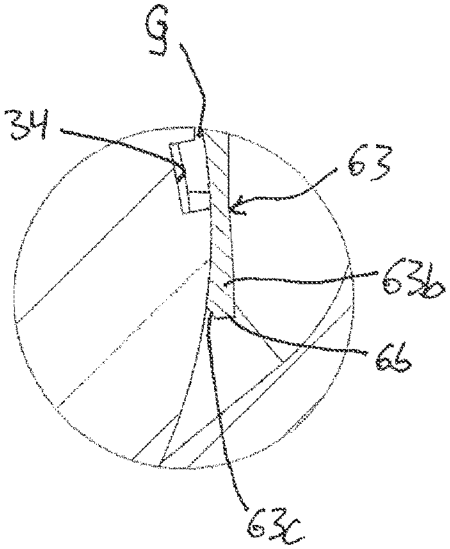
FIG. 15*b* shows an enlarged view of a detail of FIG. 15*a*.

As best seen in FIG. 14*b* and FIG. 15*b*, an end portion at an inner wall of the second section 63*b* is beveled. In other words, there is an inclined section 63*c* between the lower end 6*b* and the spherically shaped inner wall of the second section 63*b*. The inclination of the inclined section 63*c* is such that the thickness of the second section 63*b* decreases towards the bottom end 6*b*. The inclined section 63*c* may serve for facilitating disengagement between the second section 63*b* of the flaps 63 and the groove 34. The length of the flaps 63 in an axial direction is such that when the head 3 is within the spherical recess 62 and when the shank axis S of the bone anchoring element 1 coincides with the cylinder axis of the pressure member 6, or in other words, when the shank 2 is in the zero position, the second section 63*b* can extend into the groove 34.

When the pressure member 6 is placed onto the head 3, the head 3 has to pass the second spherical section 63*b* to move into the spherical recess 62, thereby slightly expanding the second spherical section 63*b*. Hence, the pressure member 6 is configured to hold the head 3 by frictional forces exerted by the flaps 63 onto the head 3.

Lastly, the pressure member 6 has a coaxial bore 65 for allowing access to the head 3, more particularly to the recess 4 of the bone anchoring element 1, with a tool.

The parts and portions of the bone anchoring device may be made of any material, preferably of titanium or stainless steel or any bio-compatible metal or metal alloy or plastic material. As a bio-compatible alloy, a NiTi alloy, for example Nitinol, may be used. Other materials that can be used are magnesium or magnesium alloys. Bio-compatible plastic materials for use may be, for example, polyether ether ketone (PEEK) or poly-L-lactide acid (PLLA). The parts can be made of the same or of different materials from one another.

The bone anchoring device may be used in a pre-assembled configuration. In the pre-assembled configuration, the head 3 of the bone anchoring element 1 is held in the seat 52 such that the head 3 can pivot within the seat 52 and the shank 2 extends through the lower opening 52*b*. The pressure member 6 can be placed on the head 3. The rod receiving recess 61 is aligned with the substantially U-shaped recess 53 of the receiving part. In this position of the pressure member, the flaps 63 are aligned with the circumferential locations of the recesses 56 in the receiving part 5. The pressure member 6 is then moved towards the bottom end 5*b* of the receiving part 5, such that the second sections 63*b* of the flaps 63 are respectively pressed over the spherical surface portion 33 including the largest diameter E of the head 3. Thereby the flaps 63 are spread slightly outward until the head 3 fits into the spherical recess 62 and the first spherical surface portions 63*a* of the flaps 63. The recesses 56 provide space for the spreading of the flaps 63.

FIGS. 14*a* to 15*b* show cross-sectional views of the bone anchoring device according to the first embodiment, where the cross-section is taken in a plane that includes the shank axis S and extends at an oblique angle to the longitudinal axis L of the U-shaped recess 53. In FIGS. 14*a* to 15*b*, a configuration is shown in which the shank may already be inserted into bone and where a rod and a fixation element are not yet inserted. As depicted in FIGS. 14*a* and 14*b*, when the shank axis S of the bone anchoring element 1 is coaxial with the central axis C of the receiving part 5 and the cylinder axis of the pressure member 6, the flaps 63 snap with their second sections 63*b* into the groove 34 of the head 3. In the predetermined position, which in this embodiment is the zero position, the shank axis S assumes an angle of 0° with the central axis C. The predetermined position is indicated or identified by the engagement of the first position indication structure in the form of the groove 34 and the second position indication structure in the form of the flaps 63.

When the second section 63*b* extends to a certain amount into the groove 34, a small radial gap G may be formed between the reduced diameter section 35 of the head 3 and an inner wall of the flaps 63.

The receiving part 5 can be pivoted relative to the inserted head 3. Pivoting the parts relative to one another to the predetermined position results in an engagement of the second spherical section 63*b* and the groove 34. Thereby a tactile and/or audible feedback signal is produced.

As shown in FIGS. 15*a* and 15*b*, when the shank 2 is moved out of the predetermined position, which in this embodiment is the zero position, the flaps 63 are spread outward and moved out of the groove 34. The inclined section 63*c* and the reduced diameter section 35 providing the gap G can each help more easily facilitate the disengagement between the flaps 63 and the groove 34. In angular positions other than the predetermined position, the first position indication structure and the second position indication structure are disengaged.

In clinical use, at least two bone anchoring devices are anchored into bone parts or vertebrae. Then, the receiving parts 5 are aligned to have a corrected or desired orientation for insertion of the rod 100. When any of the receiving parts 5 and the corresponding shanks 2 of the bone anchoring elements 1 are moved to the predetermined position, the resilient flaps 63 snap into the groove 34. The practitioner experiences a tactile and/or an audible feedback signal indicating that the parts have been adjusted to the predetermined position. This facilitates the steps of adjustment, re-adjustment, and/or correction. At any position, the head 3 is frictionally held in the receiving part so that the receiving part should not loosely pivot relative to the head. By overcoming the frictional force, the receiving parts 5 can be pivoted relative to the inserted heads 3.

Once a correct or desired orientation of the receiving part 5 relative to a bone anchoring element 1 is obtained, the rod is inserted and the locking element 7 is tightened to lock the head 3 and the rod 100 in the receiving part 5.

Figure 16A:
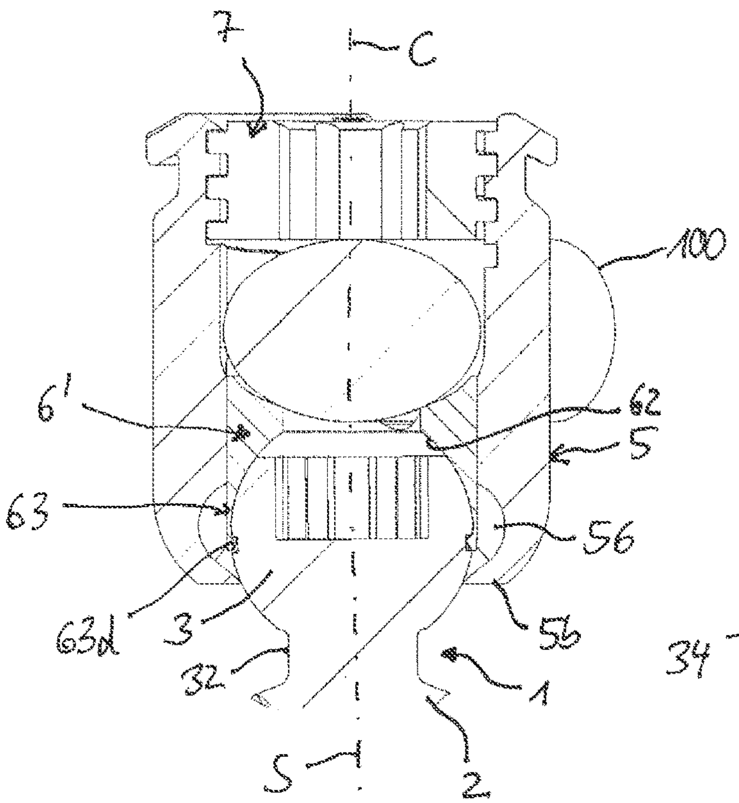
FIG. 16*a* shows a cross-sectional view of a second embodiment of the bone anchoring device, the cross-section taken in a plane that goes through centers of the head, the shank, and the receiving part, and that extends at an angle to a longitudinal axis of an inserted rod.
Figure 16B:
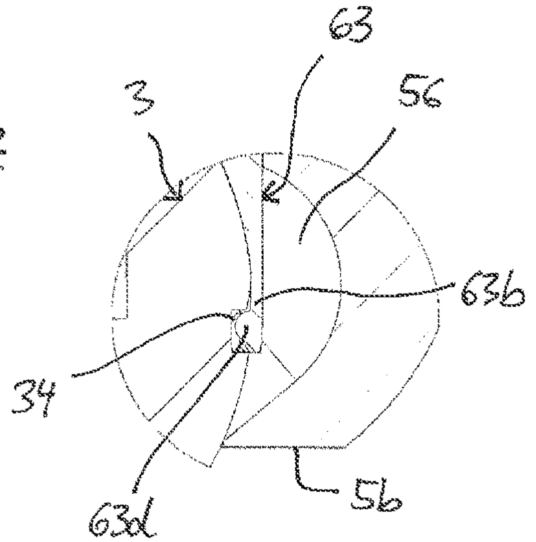
FIG. 16*b* shows an enlarged view of a detail of FIG. 16*a*.
Figure 17:
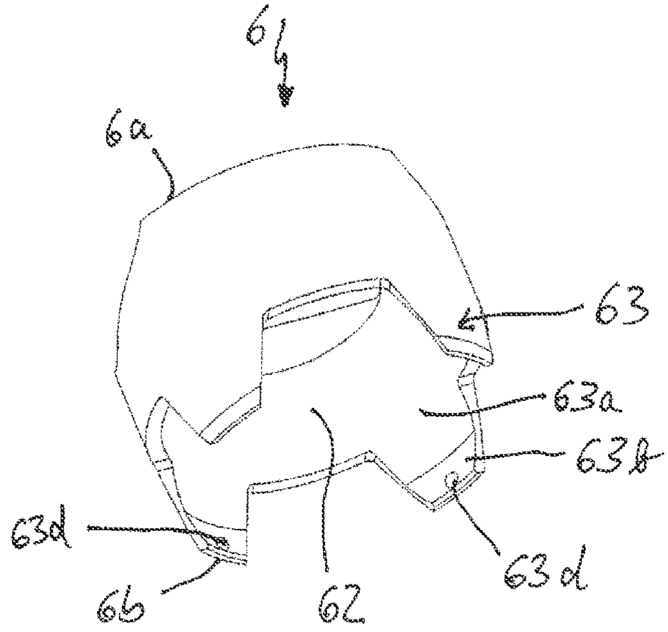
FIG. 17 shows a perspective view from a bottom of a pressure member of the bone anchoring device of FIG. 16*a*.

A second embodiment of the bone anchoring device is shown in FIGS. 16*a* to 17. The bone anchoring device according to the second embodiment differs from the bone anchoring device according to the first embodiment only with respect to the pressure member. All other parts are identical or substantially similar to the first embodiment and the descriptions thereof will not be repeated. Near the bottom end 6*b*, the pressure member 6' includes a projection 63*d* that is configured to engage the groove 34 on the head 3. The projection 63*d* is formed at the inner wall of each of the flaps 63 in the second section 63*b*. The size of the projection is such that the projection forms a distinct bulge in approximately a center of the second section 63*b* relative to the lateral edges. The shape of the projection 63*d* may be substantially like a section of a sphere. With the projection 63*d*, the holding force of the pressure member 6' in the groove 34 when the respective parts are at the predetermined position may be enhanced.

Figure 18A:
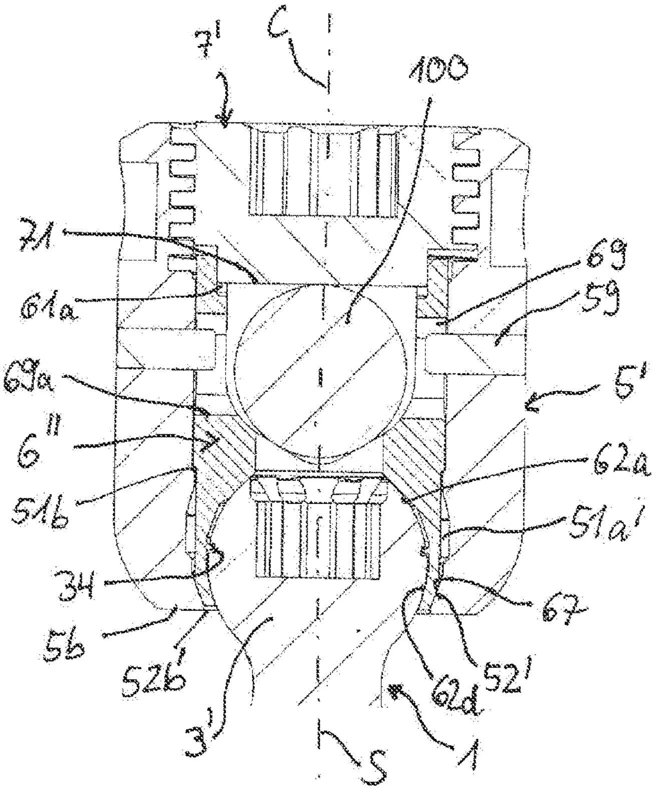
FIG. 18*a* shows a cross-sectional view of a third embodiment of the bone anchoring device, the cross-section taken in a plane that extends through a center of the bone anchoring element and centers of the legs of the receiving part, and that is arranged perpendicular to a longitudinal axis of an inserted rod.
Figure 18B:
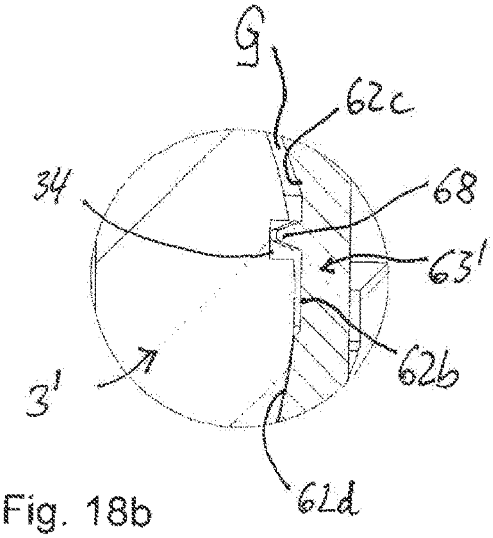
FIG. 18*b* shows an enlarged view of a detail of FIG. 18*a*.
Figure 19:
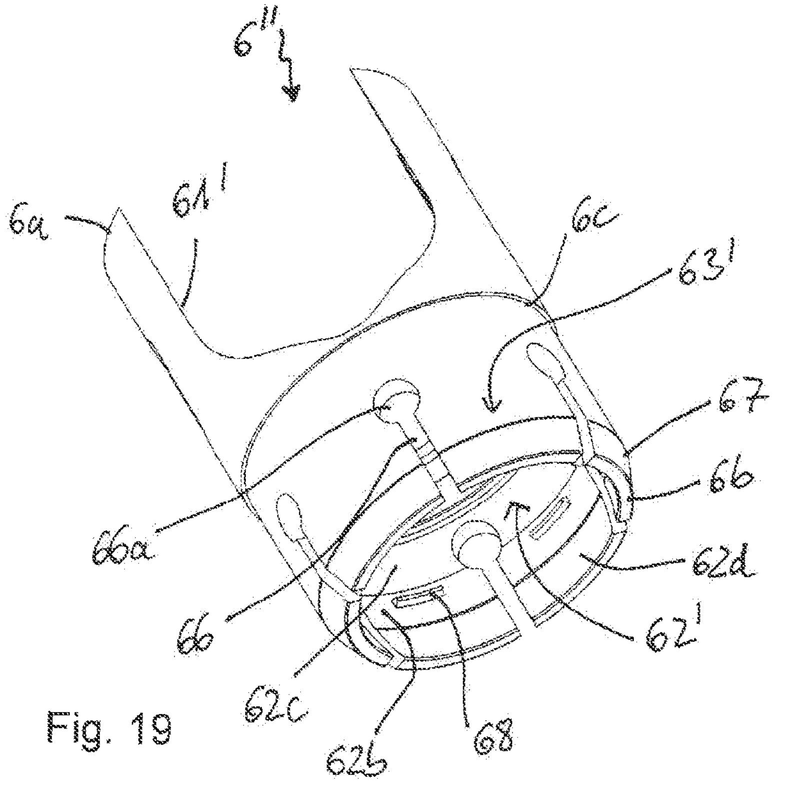
FIG. 19 shows a perspective view from a bottom of a pressure member of the bone anchoring device of FIGS. 18*a* and 18*b*.
Figure 20A:
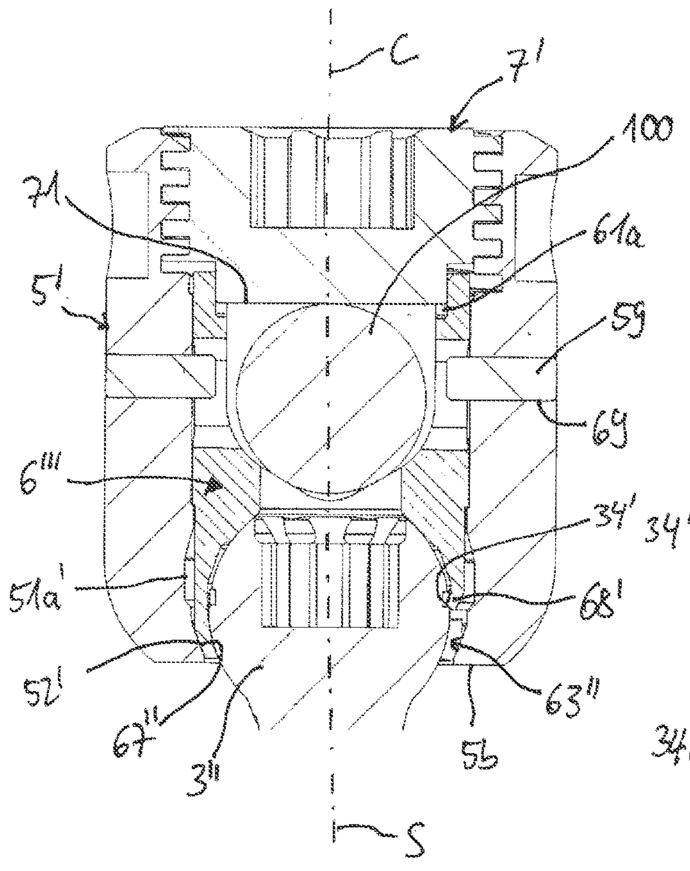
FIG. 20*a* shows a cross-sectional view of a fourth embodiment of the bone anchoring device, the cross-section taken in a plane that extends through a center of the bone anchoring element and centers of the legs of the receiving part, and that is arranged perpendicular to a longitudinal axis of an inserted rod.
Figure 20B:
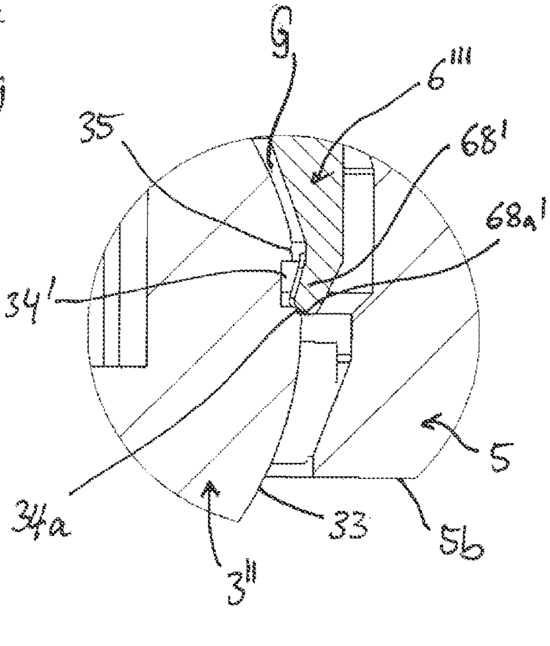
FIG. 20*b* shows an enlarged view of a detail of FIG. 20*a*.
Figure 21:
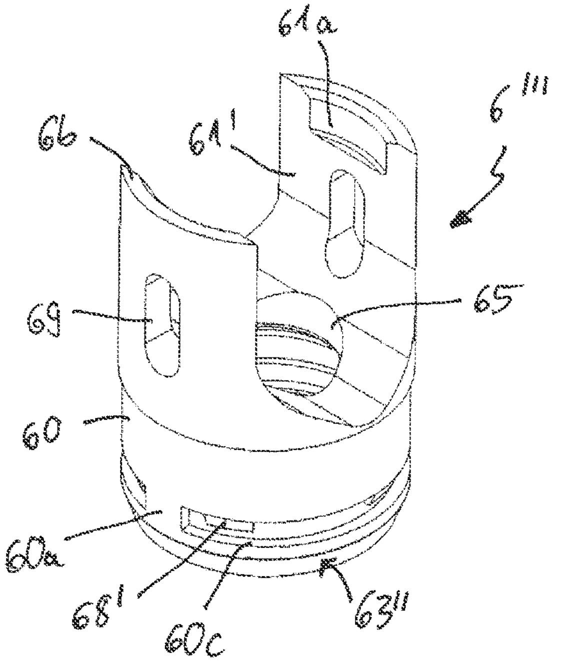
FIG. 21 shows a perspective view from a top of a pressure member of the bone anchoring device of FIGS. 20*a* and 20*b*.
Figure 22:
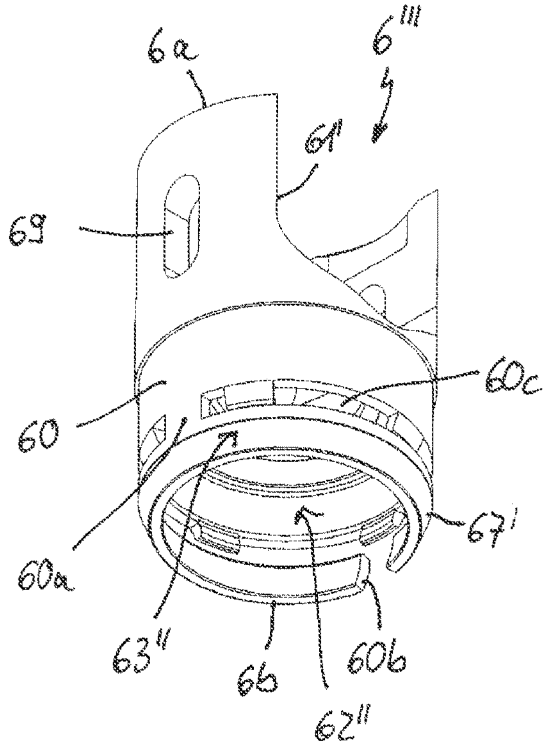
FIG. 22 shows a perspective view from a bottom of the pressure member of FIG. 21.
Figure 23:
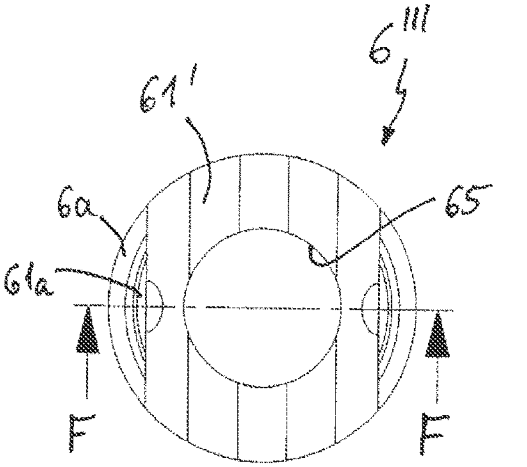
FIG. 23 shows a top view of the pressure member of FIGS. 21 and 22.
Figure 24:
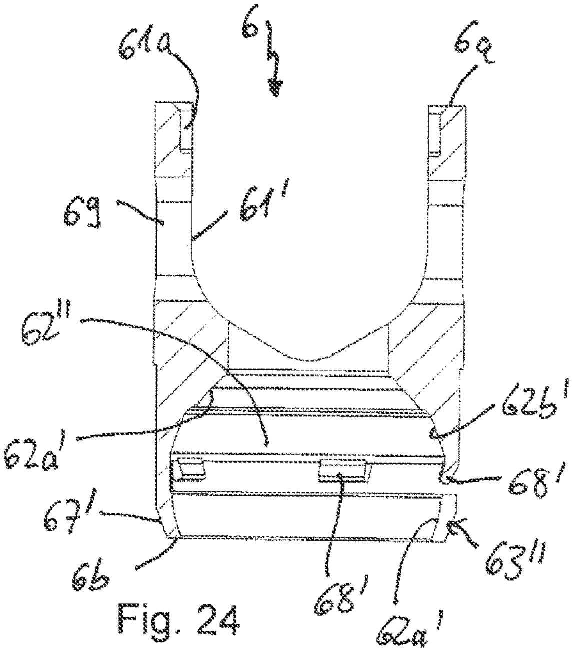
FIG. 24 shows a cross-sectional view of the pressure member of FIGS. 21 to 23, the cross-section taken along line F-F in FIG. 23.

A third embodiment of the bone anchoring device is depicted in FIGS. 18*a* to 19. The bone anchoring device according to the third embodiment is a bottom-loading polyaxial bone anchoring device. The bone anchoring device includes a receiving part 5' that is similar to the receiving part of the previous embodiments, but differs with respect to the accommodation of the head and the shapes of the pressure member and the head. The opening 52*b*' at the lower end 5*b* of the receiving part 5' has a width that is greater than the largest diameter E of the head 3', so that the head 3' can enter into the receiving part 5' from the bottom end 5*b*. Adjacent to the bottom end 5*b*, a narrowing section 52' is formed that is configured to receive a portion of the pressure member 6". The narrowing section 52' may narrow conically or narrow in another way that is suitable to exert a compression force onto the portion of the pressure member 6" that cooperates therewith. Following the narrowing portion 52' there is an accommodation space 51*a*' that provides space for the pressure member 6" to expand therein to enable insertion of the head 3' into the pressure member 6".

The head 3' differs from the head 3 of the previous embodiments in that the section 35 with reduced diameter is omitted.

The pressure member 6" has an upper portion including a recess 61' for the rod 100 and a lower portion including a head receiving recess 62'. The lower portion is substantially cylindrical and may have a slightly reduced outer width compared to the upper portion, so that a step 6*c* is formed therebetween. The lower portion includes flexible wall sections 63' that are separated by axial slots 66 which open towards a bottom end 6*b*. To obtain a certain degree of flexibility, the slots 66 may widen towards their closed end 66*a*. Adjacent to the bottom end 6*b*, the pressure member 6" has an outer tapered surface portion 67, for example conically or otherwise tapered, that is configured to cooperate with the narrowing portion 52' in the receiving part 5'. At a distance from the lower end 6*b*, a plurality of equidistantly spaced rib-like projections 68 are formed at an inner wall of the head receiving recess 62'. The projections 68 form second position indication structures that are configured to cooperate with the first position indication structure on the head 3', for example, in the form of groove 34. The projections 68 may have a substantially triangular cross-section with a rounded tip. Thereby, engagement and disengagement with the groove 34 may be more easily facilitated.

As can be seen in particular in FIGS. 18*a* and 18*b*, the head receiving recess 62' is substantially hollow spherically-shaped in a first region 62*a* which contacts the head 3 adjacent to the flat surface 31, and also substantially hollow spherically-shaped in a second region 62*d* adjacent to the bottom end 6*b*. There may be an inner cylindrical wall 62*b* that extends below the projections 68 and a conical wall 62*c* that extends above the projections 68, respectively, so that there is a gap G formed between the spherical outer surface portion 33 of the head 3 and the inner wall of the head receiving recess 62'. The gap G may facilitate easier disengagement of the projection 68 from the groove 34.

In the embodiment shown, the recess 61' has a depth such that the top end 6*a* of the pressure member 6" extends above the surface of an inserted rod 100. Transverse pins 59 extend into axially elongated recesses 69 formed in walls of the pressure member 6", as shown in FIG. 18*a*. The pins 59 form a rotation prohibiting device that prevents the pressure member 6" from rotation around the central axis C, so that the recess 61' and the substantially U-shaped recess 53 remain aligned. Moreover, the pins 59 form an axial securing device that prevent the pressure member 6" from escaping through the top end 5*a* of the receiving part 5' when the rod 100 and a locking element 7' are not inserted. The locking element 7', which may be suitable for this bone anchoring device, includes a central projection 71 that extends into a cylindrical recess 61*a* provided at a top end 6*a* of the pressure member 6". Thereby, pressure exerted by the locking element 7' acts only onto the rod 100 which in turn presses onto the pressure member 6", so that the tapered lower end section 67 of the pressure member 6" is pressed into the narrowing portion 52' of the receiving part 5'.

To prevent removal of the pressure member 6" through the lower opening 52*b*' when the head 3' is not inserted, the step 6*c* formed between the upper and lower portions of the pressure member 6" abuts against a small shoulder 51*b* at an inner passage 51 of the receiving part.

In use, the bone anchoring element 1 may be inserted first into a prepared hole in a bone or in a vertebra, and the receiving part 5' with pre-assembled pressure member 6" may then be mounted onto the head 3'. Alternatively, the bone anchoring device is pre-assembled in such a manner that the receiving part 5' with the pressure member 6" is already mounted onto the head 3' prior to insertion into a bone or vertebra. For mounting, the head 3' is inserted from the lower end 5*b* into the accommodation space 51*a*' of the receiving part 5'. The pressure member 6" is at an uppermost insertion position where the pins 59 abut against a lower end 69*a* of the elongated recesses 69. Once the head 3' has been inserted, the pressure member 6" is moved down until the outer tapered section 67 enters into the narrowing section 52' and exerts a compression force onto the head 3'. In the predetermined position of the shank 2 relative to the receiving part 5', which is a zero position in the embodiment shown, the projection 68 snaps into the groove 34. As the wall sections 63' are flexible and have space in the form of the accommodation space 51*a*' and the gap G to expand and snap back, a tactile and/or audible feedback signal is given to the user indicating that the shank 2 is in the zero position relative to the receiving part 5'. When the outer tapered section 67 is compressed in the narrowing section 52', a frictional force is exerted onto the head 3' so that the head 3' is held at any position by the friction force. Moreover, the head 3' is prevented from being removed through the opening 52*b*', since the pressure member 6" narrows the opening so that the head 3' can no longer pass therethrough. Once the receiving part 5' is pivoted relative to the shank 2, the projection 68 may be disengaged from the groove 34. This may be more easily facilitated due to the inclined sidewalls of the projection 68. The resiliency of the flexible wall sections 63' and the gap more easily permit the disengagement.

Once the shank and the receiving part are aligned at a desired position, the rod and the fixation element can be inserted and the fixation element can be tightened.

A fourth embodiment of the bone anchoring device will be described with respect to FIGS. 20*a* to 24. The bone anchoring device according to the fourth embodiment differs from the bone anchoring device according to the third embodiment in the design of the pressure member. Meanwhile, the receiving part may be substantially the same as the receiving part in the second embodiment. Identical or substantially similar parts are indicated with the same reference numerals, and the descriptions thereof will not be repeated.

It shall be noted that for this embodiment, the bone anchoring element has a head 3" with a reduced diameter section 35, similarly as seen in the first embodiment. In addition, an edge 34*a* between the outer spherical surface portion 33 and the groove 34' on a side closer to the neck 32 may be rounded.

The pressure member 6''' differs from the pressure member 6" of the third embodiment in the design of the lower portion. The upper portion may be identical to that of the pressure member 6". The lower portion of the pressure member 6"' has a cylindrical portion 60 with an outer cylindrical surface and a slotted resilient ring 63" that is adjacent to the lower end 6*b*. The resilient ring 63" is connected to the cylindrical section 60 on one side by an axial connection portion 60*a*, and is otherwise separated therefrom by a horizontal slot 60*c*. Moreover, a vertical slot 60*b* that is located at the opposite side of the connection portion 60*a* render the ring 63" resilient so that ring 63" can be expanded and compressed in the radial direction. An outer surface 67' of the ring 63" is tapered, for example conically tapered, towards the lower end 6*b*. The head receiving recess 62" of the pressure member 6"' has a first hollow spherical shape 62*a*' at the inside of the ring 63" and at the side that contacts the head 3" adjacent the end surface 31. Above the connection portion 60*a*, the inner wall of the head receiving recess 62" has a conically shaped section 62*b*'. At the lower end of the conically shaped section 62*b*', a plurality of equidistantly spaced and circumferentially extending rib-like projections 68' are formed that project downward and inward towards a central axis of the head receiving recess 62". In the embodiment, four such projections 68' are provided. One of the projections 68' may be located above the slot 60*b*, while another one of the projections 68' may be formed on the connection portion 60*a*. The projections 68' each has a rounded beveled free end 68*a*'. As depicted in greater detail in FIGS. 20*a* and 20*b*, the rounded free end 68*a*' can contact the wall of the groove 34' at the rounded edge 34*a*. In the predetermined position, which is in this embodiment a zero position, the projections 68' rest on the edge 34*a* of the wall of the groove 34 and extend only to a certain extent into the groove 34'.

In use, the pressure member 6"' may be pre-assembled with the receiving part 5'. The head 3" is inserted from the lower end 5*b*. When the pressure member 6"' is in its uppermost position, which is an insertion position, the ring 63" is located in the accommodation space 51*a*' such that the ring 63" can expand and snap over the head 3". When the projections 68' engage the groove 34' and rest on the edge 34*a*, a tactile and/or audible feedback signal is given to the user. Pivoting the head 3" causes the projections 68' to be bent outwards slightly so that the head 3" can move to another angular position and may then be held at the other angular position by friction. The ring 63" contributes to the frictional clamping of the head 3" and prevents falling out of the head 3" through the lower opening 52*b*'.

Once the shank and the receiving part are aligned at a desired angular position, the rod and the fixation element can be inserted and the fixation element can be tightened. To lock the head 3" and the rod 100, the locking element 7' is tightened so that the locking element 7' presses onto the rod 100, which in turn presses onto the pressure member 6"'.

It shall also be noted that a two-part locking element can be used, which has an outer locking element that acts onto the top end 6*a* of the pressure member 6" of the third embodiment or the pressure member 6"' of the fourth embodiment, and an inner locking member that can be advanced in the first locking member and which acts on the rod. Thereby, separate locking of the head and the rod can be achieved.

Figure 25A:
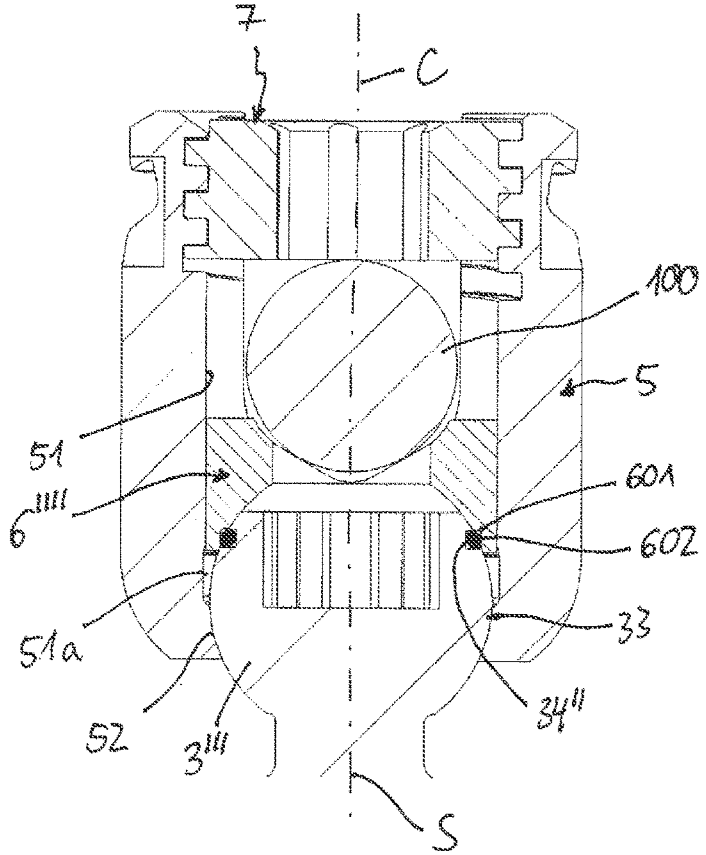
FIG. 25*a* shows a cross-sectional view of a fifth embodiment of the bone anchoring device, the cross-section taken in a plane that extends through a center of the bone anchoring element and centers of the legs of the receiving part, and that is arranged perpendicular to a longitudinal axis of an inserted rod.
Figure 25B:
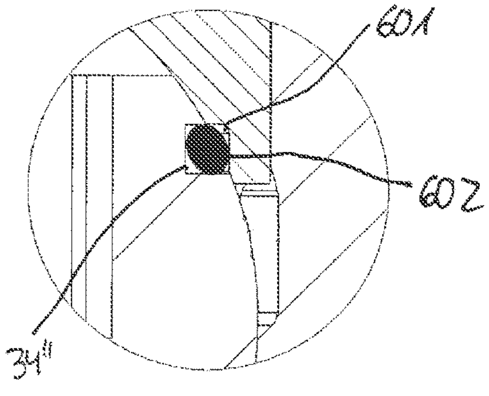
FIG. 25*b* shows an enlarged view of a detail of FIG. 25*a*.
Figure 26:
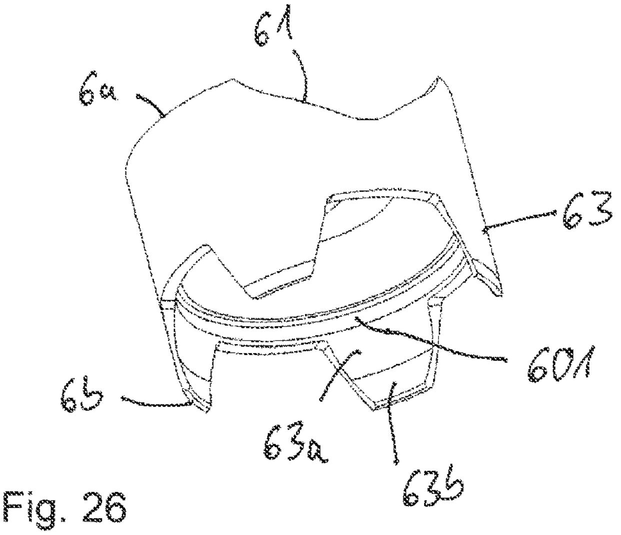
FIG. 26 shows a perspective view from a bottom of a pressure member of the bone anchoring device of FIGS. 25*a* and 25*b*.

A fifth embodiment will be described with respect to FIGS. 25*a* to 26. The bone anchoring device according to the fifth embodiment includes a receiving part 5 that is similar to the receiving part 5 of the first embodiment, intended to be a receiving part for a top-loading polyaxial bone anchoring device. The receiving part 5 has a seat 52 for the head, which has a spherical shape in this embodiment, but can have any other shape in other embodiments that provides a ball and socket joint. The recesses 56 shown in the first embodiment can be omitted. The passage 51 may extend down to the seat 52 in a constant width, or may have a widened section in other embodiments. The head 3"' includes the first position indication structure in the form of a groove 34". The groove 34" is provided in the upper portion of the head 3"'. In greater detail, the groove 34" is located above the section of the head with the largest diameter E. Preferably, the groove 34" is provided closer to the end surface 31 of the head 3"' than to the section of the head with the greatest diameter E. Due to the spherical outer surface 33 of the head, the sidewalls of the groove 34" have different lengths in the radial direction.

The pressure member 6"" is similar to the pressure member of the first embodiment. The pressure member 6"" has flaps 63 that have a length such that when the pressure member 6"" is placed onto the head, upper ends of the flaps 63 extend below the groove 34". At an inner wall of the spherical head receiving recess 62 of the pressure member 6"" and above the flaps 63, a circumferential recess 601 with a substantially triangular cross-section is formed. When the pressure member 6"" is placed onto the head 3, the flaps 63 effect a friction hold of the head 3"' and the recess 601 covers the groove 34". A resilient ring 602 is provided in the groove 34". The cross-section of the ring 602 may be oval-shaped. The resilient ring 602 may be made, for example, of a bio-compatible polymer, such as certain polyurethanes. Alternatively, the resilient ring may be a slotted ring. By means of this, the groove 34" and the resilient ring 602 form the first position indication structure and the corresponding recess 601 on the pressure member 6"" forms the second position indication structure.

In use, when the bone anchoring device is assembled, the resilient ring 602 effects a resistance when the head 3"' is pivoted out of the predetermined position, which in this embodiment is a zero position of the shank relative to the receiving part. Thereby a tactile and/or audible feedback signal may be generated. The clinical use can be similarly as described with the bone anchoring device of the first embodiment. Once the shank and the receiving part are aligned at a desired angular position, the rod and the fixation element can be inserted and the fixation element can be tightened.

Further modifications of the embodiments described above are also conceivable. The features of one embodiment can be combined with those of other embodiments to provide a variety of further embodiments. Receiving parts according to the invention are not limited to the receiving parts shown with respect to the various embodiments described. As a main interaction is between the head and the pressure member, all known receiving parts may be used and retrofitted with suitable bone anchoring elements and pressure members that have first and the second position indication structures. In addition, position indication structures are not limited to only indicating a zero position. In other embodiments of the invention, position indication structures can also be used to indicate another predetermined angular position in which the shank assumes an angle different from the zero position with respect to the receiving part. For example, the groove may be oblique with respect to the central axis, and the projections engaging the groove may be provided at different heights in the axial direction. In addition, the grooves and projections may be interchanged, so that the projections are provided on the head and the groove or grooves are provided on the pressure member.

While the head is shown to be a spherical head and the pressure member is shown to have a spherical head receiving recess, bone anchoring devices according to the invention also are not limited thereto. It is conceivable, for example, that in other embodiments, the head and the pressure member are shaped so as to permit angulation in one or more distinct planes only.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A bone anchoring device comprising:

an anchoring element having a shank for anchoring in a bone and a head that has a spherical segment-shaped outer surface and a first recessed portion that is recessed from the outer surface, wherein the head is devoid of any other recessed portions that have a similar cross-sectional profile as the first recessed portion;

a receiving part having a first end, a second end below the first end, and a central axis that extends between the first and second ends, and defining a coaxial passage configured to pivotably receive the head such that the shank extends away from the second end and can assume a plurality of angular positions relative to the receiving part; and a pressure member positionable above the head and movable in the passage, the pressure member comprising a pressure exerting surface for exerting pressure on the head to clamp the head in the receiving part and an engagement surface;

wherein the shank is configured to assume a first angular position from among the plurality of angular positions relative to the receiving part where the engagement surface of the pressure member extends at least partially into the first recessed portion of the head, and wherein the shank is pivotable away from the first angular position while an axial position of the pressure member relative to the receiving part remains constant to disengage the engagement surface from the first recessed portion.

2. The bone anchoring device of claim 1, wherein the engagement surface is configured to engage the first recessed portion in a resilient manner.

3. The bone anchoring device of claim 1, wherein the engagement surface of the pressure member comprises a projection.

4. The bone anchoring device of claim 1, wherein the first angular position is a zero angle where a longitudinal axis of the shank and the central axis of the receiving part are substantially coaxial.

5. The bone anchoring device of claim 1, wherein a tactile feedback signal is generated when the engagement surface engages the first recessed portion.

6. The bone anchoring device of claim 1, wherein the recessed portion is formed by a circumferentially extending groove formed in the outer surface of the head.

7. The bone anchoring device of claim 1, wherein when the engagement surface of the pressure member remains engaged with the head but is spaced apart from the recessed portion, the engagement surface is only configured to engage the spherically-shaped portion of the outer surface.

8. The bone anchoring device of claim 1, wherein the recessed portion of the head is recessed from the spherically-shaped portion of the outer surface by a first depth, and wherein the head is devoid of any other recessed portions that are recessed from the spherically-shaped portion of the outer surface by at least the first depth.

9. The bone anchoring device of claim 1, wherein at least part of the recessed portion is formed by a conical surface.

10. A bone anchoring device comprising:

an anchoring element having a shank for anchoring in a bone and a head that has a spherical segment-shaped outer surface and a first recessed portion that is recessed from the outer surface, wherein the head is devoid of any other recessed portions that have a similar cross-sectional profile as the first recessed portion;

a receiving part having a first end, a second end below the first end, and a central axis that extends between the first and second ends, and defining a coaxial passage configured to pivotably receive the head such that the shank extends away from the second end and can assume a plurality of angular positions relative to the receiving part; and a pressure member positionable above the head and movable in the passage, wherein part of the pressure member is configured to extend below a portion of the head having a greatest width measured in a direction perpendicular to the central axis;

wherein the shank is configured to assume a first angular position from among the plurality of angular positions relative to the receiving part where an engagement surface of the bone anchoring device extends at least partially into the first recessed portion of the head, and wherein the shank is pivotable away from the first angular position to disengage the engagement surface from the first recessed portion.

11. The bone anchoring device of claim 10, wherein the engagement surface is formed on the pressure member.

12. The bone anchoring device of claim 10, wherein the part of the pressure member that is configured to extend below the portion of the head having the greatest width is radially expandable.

13. The bone anchoring device of claim 10, wherein the first angular position is a zero angle where a longitudinal axis of the shank and the central axis of the receiving part are substantially coaxial.

14. The bone anchoring device of claim 10, wherein the recessed portion is formed by a circumferentially extending groove formed in the outer surface of the head.

15. The bone anchoring device of claim 10, wherein at least part of the recessed portion is formed by a conical surface.

16. A bone anchoring device comprising:

an anchoring element having a shank for anchoring in a bone and a head that has an outer surface and a recessed portion that is recessed from the outer surface;

a receiving part having a central axis and defining a coaxial passage configured to pivotably receive the head such that the shank can assume a plurality of angular positions relative to the receiving part; and a pressure member positionable above the head and movable in the passage, the pressure member comprising an engagement surface and a pressure exerting surface having a shape that matches a shape of part of the outer surface of the head;

wherein the shank is configured to assume a first angular position from among the plurality of angular positions relative to the receiving part where the engagement surface of the pressure member extends at least partially into the first recessed portion of the head, and wherein the shank is pivotable away from the first angular position to a second angular position from among the plurality of angular positions relative to the receiving part to disengage the engagement surface from the first recessed portion; and wherein at least part of the matching surfaces of the outer surface of the head and the pressure exerting surface of the pressure member contact one another when the shank assumes both the first angular position and the second angular position.

17. The bone anchoring device of claim 16, wherein the shank is pivotable away from the first angular position to the second angular position while a cross-sectional profile of the pressure member remains constant.

18. The bone anchoring device of claim 16, wherein the first angular position is a zero angle where a longitudinal axis of the shank and the central axis of the receiving part are substantially coaxial.

19. The bone anchoring device of claim 16, wherein at least part of the recessed portion is formed by a conical surface.

20. The bone anchoring device of claim 16, wherein the matching surfaces of the outer surface of the head and the pressure exerting surface of the pressure member are spherical segment-shaped.

* * * * *